United States Patent
LaBorde

(10) Patent No.: US 10,482,216 B2
(45) Date of Patent: Nov. 19, 2019

(54) PROTECTED HEALTH INFORMATION IMAGE CAPTURE, PROCESSING AND SUBMISSION FROM A CLIENT DEVICE

(71) Applicant: David LaBorde, Tucker, GA (US)

(72) Inventor: David LaBorde, Tucker, GA (US)

(73) Assignee: ICONIC DATA INC., Norcross, GA (US)

( * ) Notice: Subject to any disclaimer, the term of this patent is extended or adjusted under 35 U.S.C. 154(b) by 923 days.

(21) Appl. No.: 15/003,693

(22) Filed: Jan. 21, 2016

(65) Prior Publication Data

US 2016/0154941 A1 Jun. 2, 2016

Related U.S. Application Data

(63) Continuation-in-part of application No. 14/228,723, filed on Mar. 28, 2014.

(60) Provisional application No. 61/806,186, filed on Mar. 28, 2013.

(51) Int. Cl.

| | |
|---|---|
| *G16H 10/60* | (2018.01) |
| *G06F 19/00* | (2018.01) |
| *G06F 3/0484* | (2013.01) |
| *G06F 21/62* | (2013.01) |
| *G16H 40/20* | (2018.01) |
| *H04W 12/02* | (2009.01) |
| *H04W 88/02* | (2009.01) |
| *H04L 29/06* | (2006.01) |
| *H04W 12/06* | (2009.01) |

(52) U.S. Cl.
CPC ........ *G06F 19/328* (2013.01); *G06F 3/04842* (2013.01); *G06F 21/6245* (2013.01); *G16H 40/20* (2018.01); *H04L 63/0861* (2013.01); *H04W 12/02* (2013.01); *H04W 12/06* (2013.01); *H04W 88/02* (2013.01)

(58) Field of Classification Search
CPC .............................. G16H 40/20; G06F 19/328
See application file for complete search history.

(56) References Cited

U.S. PATENT DOCUMENTS

| | | | |
|---|---|---|---|
| 5,579,393 A | 11/1996 | Conner | |
| 7,353,238 B1 | 4/2008 | Gliklich | |
| 2001/0032215 A1 | 10/2001 | Kyle | |
| 2002/0019749 A1 | 2/2002 | Becker et al. | |
| 2002/0123907 A1* | 9/2002 | Strayer | G06F 19/328 705/2 |
| 2002/0198829 A1* | 12/2002 | Ludwig | G06Q 20/04 705/40 |
| 2003/0074273 A1* | 4/2003 | Miller | G06Q 30/06 705/26.1 |
| 2005/0251417 A1* | 11/2005 | Malhotra | G06Q 50/22 705/2 |
| 2005/0288965 A1 | 12/2005 | Van Eaton | |
| 2006/0053034 A1 | 3/2006 | Hlathein | |
| 2006/0229911 A1* | 10/2006 | Gropper | G06F 19/321 705/2 |

(Continued)

*Primary Examiner* — John A Pauls
(74) *Attorney, Agent, or Firm* — Culpepper IP, LLLC; Kerry S. Culpepper

(57) ABSTRACT

A system and method that permits a user to utilize a means of capturing and managing one or more images containing protected health information (PHI) on a mobile device, as disclosed herein. The user of the system and method may be required to undergo authentication and authorization to access the system and use the method.

20 Claims, 16 Drawing Sheets

(56) References Cited

U.S. PATENT DOCUMENTS

| | | |
|---|---|---|
| 2007/0143148 A1 | 6/2007 | Kol |
| 2007/0188774 A1* | 8/2007 | Yudasaka ............ H04N 1/00161 |
| | | 358/1.2 |
| 2008/0133269 A1 | 6/2008 | Ching |
| 2009/0132586 A1 | 5/2009 | Napora |
| 2009/0164236 A1 | 6/2009 | Gounares |
| 2009/0299743 A1* | 12/2009 | Rogers ............ H04M 1/274516 |
| | | 704/235 |
| 2010/0122179 A1 | 5/2010 | Nakamura |
| 2010/0161345 A1 | 6/2010 | Cain |
| 2010/0305966 A1 | 12/2010 | Coulter |
| 2011/0110568 A1 | 5/2011 | Vesper |
| 2011/0153351 A1 | 6/2011 | Vesper |
| 2012/0173281 A1 | 7/2012 | DiLella |
| 2013/0054260 A1 | 2/2013 | Evans |
| 2013/0096938 A1* | 4/2013 | Stueckemann ......... G06F 19/34 |
| | | 705/2 |
| 2013/0307955 A1 | 11/2013 | Deitz |
| 2014/0249860 A1* | 9/2014 | Rynchek ............... G06F 19/328 |
| | | 705/3 |

\* cited by examiner

Physician / provider professional services billing (charge capture) application of secure HIPAA compliant transmission and processing of image data.

Capture and entry of patient insurance information from healthcare facility face sheet for provider professional services medical billing (medical claim generation)

PROTECTED HEALTH INFORMATION IMAGE CAPTURE, PROCESSING AND SUBMISSION FROM A CLIENT DEVICE

STATEMENT OF RELATED APPLICATIONS

The present application is a continuation-in-part of U.S. patent application Ser. No. 14/228,723 filed on Mar. 28, 2014, which claims the benefit of U.S. Provisional Patent Application No. 61/806,186 filed on Mar. 28, 2013, the contents both of which are incorporated herein by reference.

TECHNICAL FIELD

The technical field relates generally to one or more client devices, manager devices and servers, and, more particularly, to a system for capturing, processing and extracting protected health information data from image and/or voice data at the client device and storing it at a database at the servers.

BACKGROUND

Protected Health Information (PHI) is defined by the US Health Insurance Portability and Accountability Act (HIPAA). The US government generally requires that systems accessing electronic health records need to be configured to grant access to PHI only to people who need to know it. If PHI is accessed by a person not authorized to access it, then this could indicate a violation of both the HIPAA Privacy and Security Rules. Under certain circumstances, such an incident may have to be reported to the US Department of Health and Human Services (HHS) and/or a state agency as a breach of unsecured protected health information. Having good access controls and knowledge of who has viewed or used information (i.e., access logs) can help to prevent or detect these data breaches.

Traditional means of data exchange or interfaces between organizations consist of in person verbal communication, wired telephone and facsimile communication, paper based communication (i.e., mail or courier service), or email communication, text messaging, an application programming interface, among others.

SUMMARY

In view of the above concerns, the present disclosure provides a solution for enabling capture and submission of information regarding medical services rendered from any location via multiple modalities available on a client device such as a mobile device, including. The mobile technology solution is a component of a broader platform that includes backend endpoints that communicate with mobile devices equipped with multiple peripherals including, but not limited to, a touch screen, a camera or video recorder, a microphone, a transceiver, controller and instructions for configuring the controller stored in a memory.

The platform enables on-the-go healthcare providers to immediately or in a queued or batched process submit via the mobile device data including, but not limited to, patient demographic, diagnosis, and billing information to a charge capture manager device at a backend endpoint that enables (i) staff members in a back office location to access, edit, and further annotate the data set via another client device; (ii) a $3^{rd}$ party system (for example, a practice management software, a claims clearing house, or a payor organization) to securely access or be sent all or a subset of the data; and (iii) the data to be sent on for further downstream processing by a machine and or human. Such data can include medical diagnosis and billing codes, health insurance information, charting related to what service(s) were rendered, etc.

The system according to one embodiment includes a charge capture client device, a manager device and one or more server devices for providing protected health information image capture, processing and submission. The client device can be implemented in a mobile device such as a smart phone which can be operated by a user as follows:

1. Use an image recording device on the mobile device to take a photograph of the key demographics of the patient (name, date of birth, account number, medical record number, gender, etc. or generally patient identification information), often from a patient sticker or a hospital facesheet;

2. Allow a user to make additional annotations to this information (description of services rendered and/or the actual diagnosis and billing codes, location of the services, etc.);

3. Securely parse this patient identification information (locally on the device or in a remote data center associated with the server) and transmit it to the charge capture manager device where it is stored securely at rest in a charge database at the server;

4. Process this information to turn the data in the image to structured data persisted in data transport objects (data sets) in the charge database; and 5. Transmit, provide access to, or present the information for consumption in a downstream business process, i.e., creating a medical claim. This can range from allowing an employee or medical billing staff member to pull up the information (i.e., look at it on a screen) from the charge database via the charge capture manager device to sending the information via an application programming interface or via a standard communications protocol like HL7 or Electronic Data Interchange (EDI) transaction (i.e., an EDI 5010 transaction) to a downstream system (i.e., a practice management software or a claims clearing house).

A user of the client device undergoes authentication and authorization to use the system. After authentication, a user can captures images containing PHI on the client device. Preferably, communication between the client device and the charge capture devices is encrypted and via a secure wired or unwired communication medium and/or protocol (if and when a connection is confirmed to be available). The data can be communicated in real-time or via a queued or batched process either standalone or as annotation to a broader dataset. The manager device or data center associated with the server can perform PHI image processing to parse the PHI from the images, which is displayed on the client device. The client device can maintain a local encrypted copy of images for some period of time or delete the data after confirming successful transmission to the manager device. The images and/or some or all of the meaningful content of the PHI image derived after PHI image processing can be stored at the charge database associated with the manager device. The manager device securely logs (for future audit purposes) any and all access to or transmission of the data after post PHI image processing. The manager device can further authenticated and authorize third parties for accessing the data related to the PHI image.

DETAILED DESCRIPTION OF PREFERRED EMBODIMENTS

In overview, the present disclosure concerns a system for providing a charge capture platform. In the system, one or more client devices and servers provide secure storage and access of patient data across different facilities. The charge capture platform is a HIPAA compliant component of a mobile technology solution that enables healthcare providers and health care provider organizations to improve provider workflow, capture more revenue and obtain payment faster in the revenue cycle and eliminating inefficiencies, interim steps, and delays in information gathering (from multiple sources and physical locations) and submission The instant disclosure is provided to further explain in an enabling fashion the best modes of performing one or more embodiments of the present invention. The disclosure is further offered to enhance an understanding and appreciation for the inventive principles and advantages thereof, rather than to limit in any manner the invention. The invention is defined solely by the appended claims including any amendments made during the pendency of this application and all equivalents of those claims as issued.

It is further understood that the use of relational terms such as first and second, and the like, if any, are used solely to distinguish one from another entity, item, or action without necessarily requiring or implying any actual such relationship or order between such entities, items or actions. It is noted that some embodiments may include a plurality of controllers/processes or steps, which can be performed in any order, unless expressly and necessarily limited to a particular order; i.e., processes or steps that are not so limited may be performed in any order.

Reference will now be made in detail to the accompanying drawings. Wherever possible, the same reference numbers will be used throughout the drawings to refer to the same or like parts.

Figure 1:
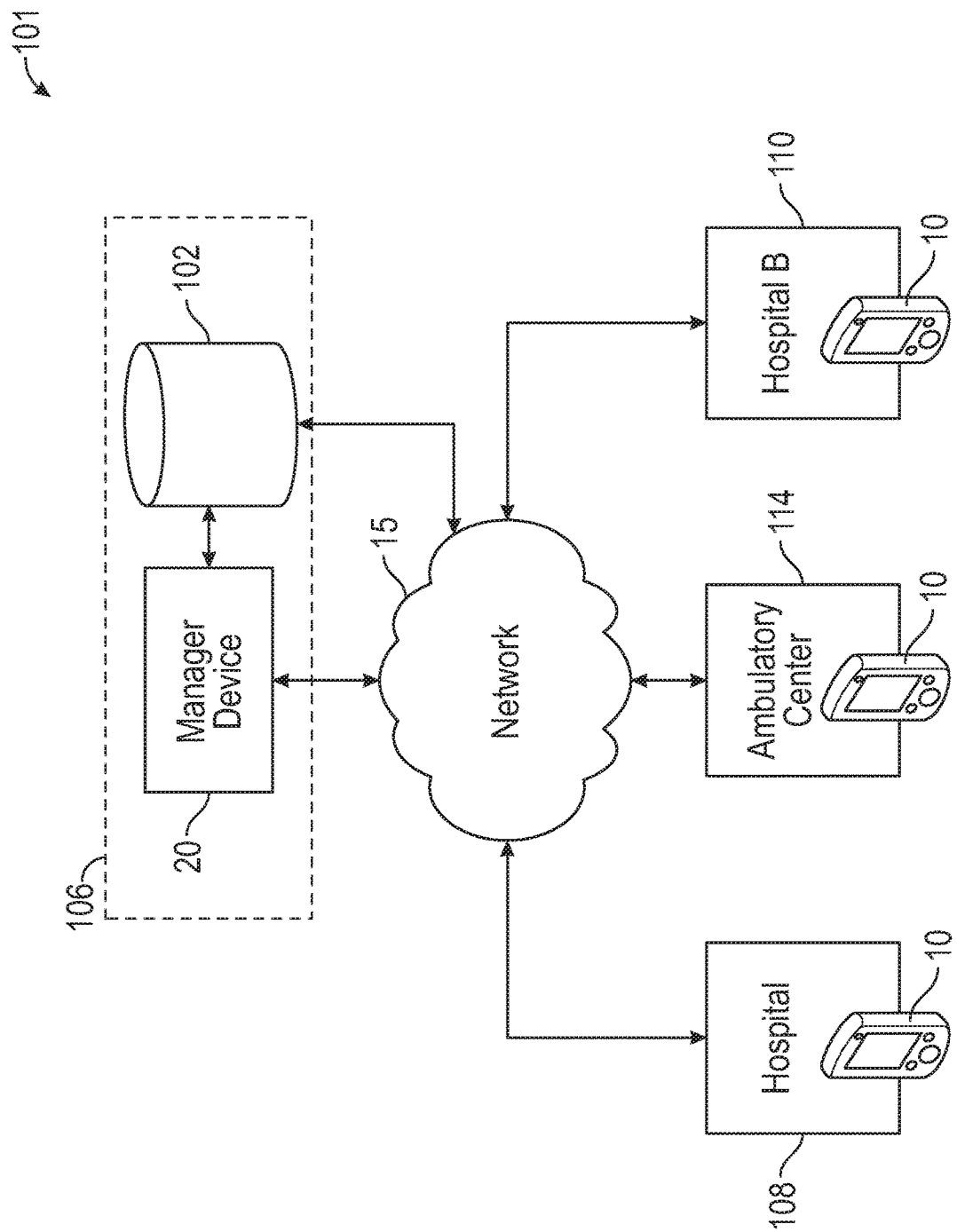
FIG. 1 illustrates an exemplary environment in which the system according to various exemplary embodiments can be implemented.

Referring to FIG. 1, a simplified and representative exemplary environment in which the system can be implemented will be discussed and described. The exemplary environment includes three facilities: a first hospital 108, a second hospital 110, and an ambulatory center 114. A client device such as smartphone 10 connected to a network 105 such as a LAN, the Internet, or a cellular network may be at either of these facilities. One or more servers represented generally by 106 provide a charge capture manager device 20 and various databases (depicted by single database 102) which are also connected to the network 15. The connection to the network 15 can be a direct connection such as a wired or wireless connection or can be an indirect connection such as a connection through the Internet, local area network, wide area network, communication network, etc. Further, although the servers were shown merely by dotted box 106, those of skill in the art should appreciate that server 106 can represent entities necessary for providing cloud computing such as infrastructure and services providers.

At each point of care in which the user such as a physician or other provider renders services (either of 108, 110, 114, for example), the user logins to a website associated with the manager device 20 via the client device 10 or accesses a client specific application to view, abstract and capture structured data about each care episode. The user or other authorized entities can then access the information captured in real time and/or near real time anytime, anywhere and utilize it to better care for their patients and improve the efficiency of their practice's operations. The client device and server of the system will be discussed in detail.

Figure 2A:
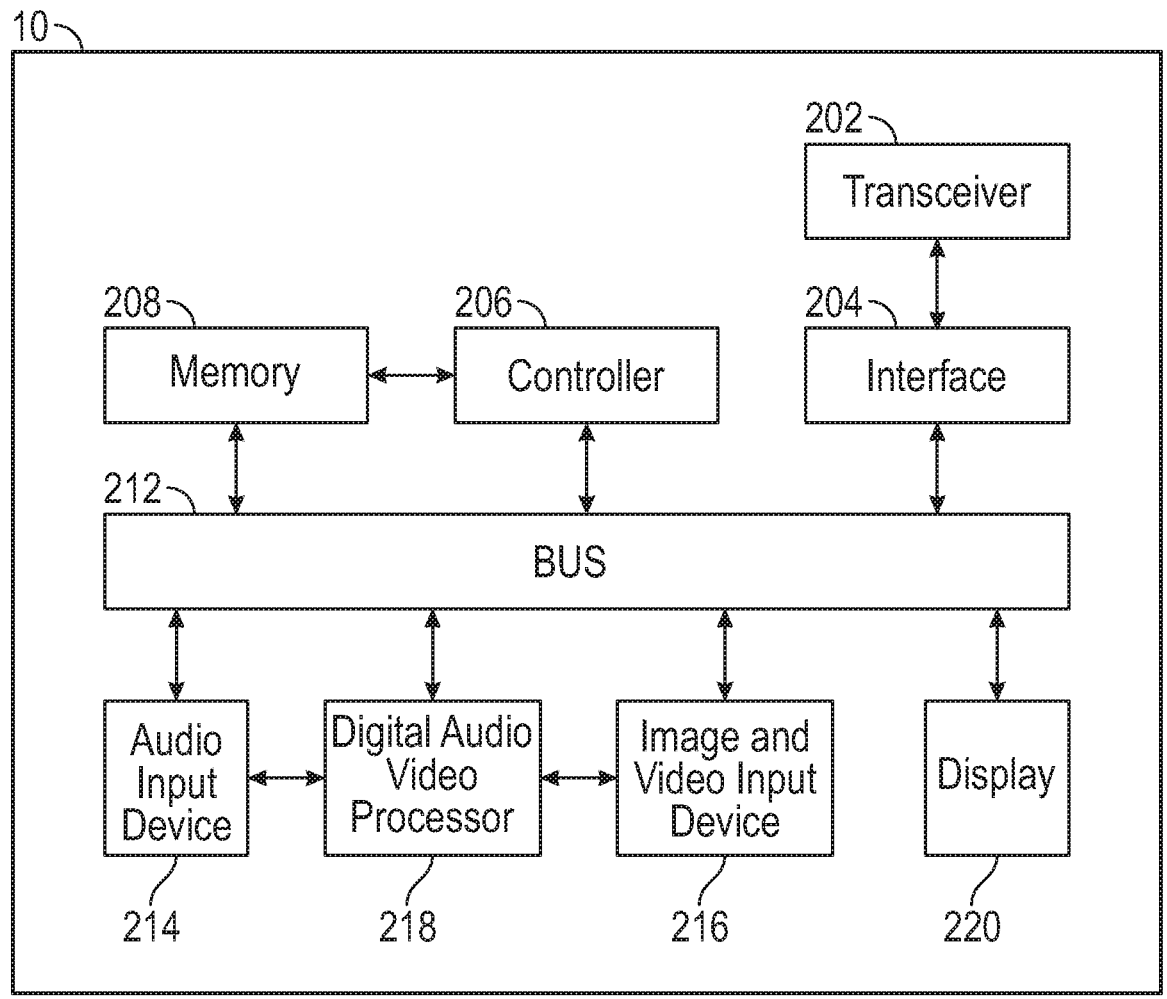
FIG. 2A is a block diagram illustrating exemplary portions of a charge capture client device according to an exemplary embodiment.
Figure 2B:
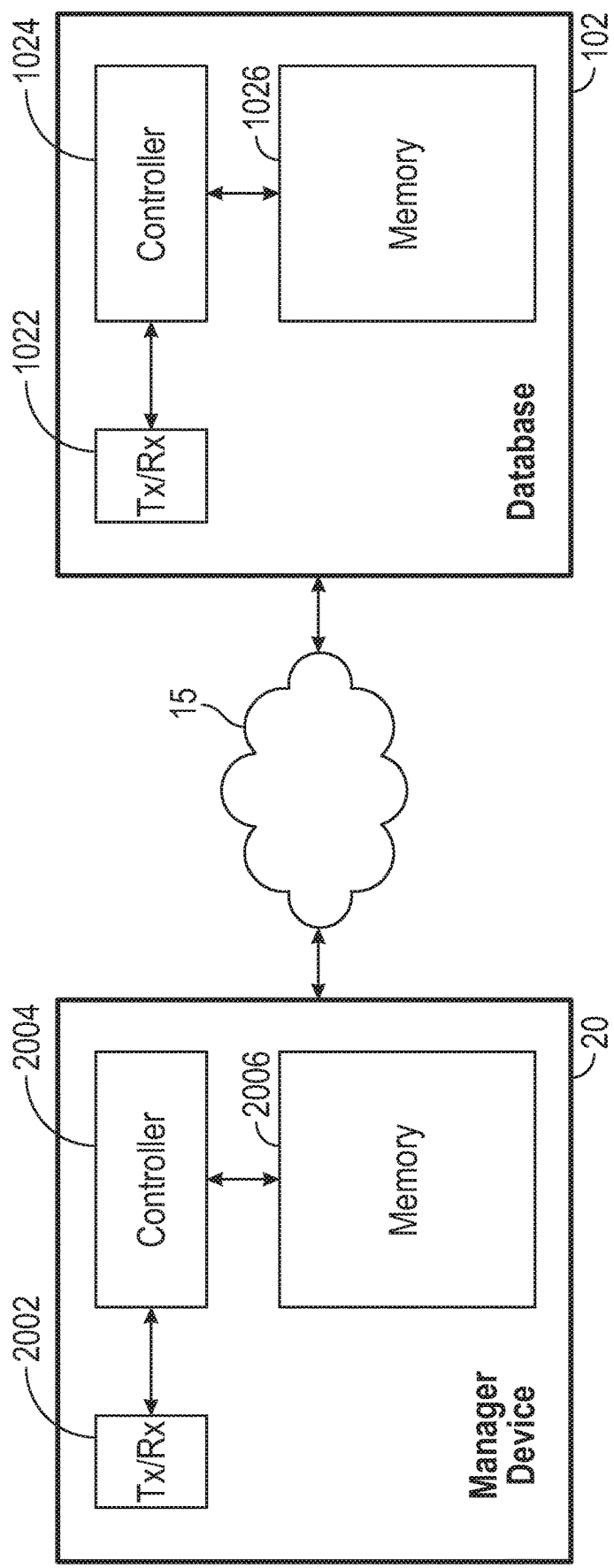
FIG. 2B is a block diagram illustrating exemplary portions of a charge capture manager device and database according to the exemplary embodiment.

Referring to FIG. 2A, the client device 10 can include a transceiver 202, an interface 204, a controller 206, a memory 208, an audio input device 214, an image and video input device 216, a digital and audio video processor 218, a display 220, and a common bus 212. Referencing the Open Systems Interconnection reference model (OSI model), the transceiver 202 provides the physical layer functions such as modulating packet bits into electromagnetic waves to be transmitted and demodulating received waves into packet bits to be processed by higher layers. The transceiver 202 can include radio technology 20 circuitry such as, for example, ZigBee, Bluetooth and WiFi. The transceiver 202 may also include Ethernet and a USB connection. Further, the transceiver 202 can include an antenna portion capable of receiving and transmitting the electromagnetic waves from and to, for example, network 15. The antenna portion can also be separate from the transceiver 202. The antenna portion can include, for example, an RF antenna, a coil antenna and/or a capacitive plate antenna.

The interface 204 can provide the data link layer and network layer functions of the client device 10 such as formatting the packet bits to an appropriate format for transmission by the transceiver 202 or received packet bits into an appropriate format for processing by the controller 206. For example, the interface 204 can be configured in accordance with the 802.11 media access control (MAC) protocol and the TCP/IP protocol. According to the MAC protocol, packet bits are encapsulated into frames for transmission and the encapsulation is removed from received frames. According to the TCP/IP protocol, error control is introduced and addressing to ensure end to end delivery. Although shown separately here for simplicity, it should be noted that both the interface 204 and the transceiver 202 may be implemented by a network interface consisting of a few integrated circuits.

The memory 208 can be one or a combination of a variety of types of memory or computer readable medium such as random access memory (RAM), read only memory (ROM), flash memory, dynamic RAM (DRAM), hard disk drive (HDD) or any type of non-transitory memory. The memory 208 generally includes instructions for configuring the controller 206 as well as a basic operating system, executable code, and data and variables. The bus 212 is a common bus for providing communications between the portions of the client device 10 with the controller 306.

The display 220 can be a conventional touch display unit for inputting text and displaying transcribed text and the various graphical displays discussed later. The audio input device 214 can include a microphone internal to the client device 10 and/or a connection for an external microphone and a processor for processing the sound signal.

The image and video input device 216 can include a video camera or be coupled to an external camera to generate images and digital video. The video input device 216 can include a CCD image sensor that generates image information by capturing a subject image formed through a lens tube. Light from the subject that becomes an object to be captured passes through the lens tube and then forms an image on the light reception surface of the CCD image sensor. The formed subject image can be converted into R, G, or B color information. As a result of the conversion, image information that indicates an entire subject image is generated. The CCD image sensor can generate image information of a new frame at each constant time. The video input device 216 can include an 8 megapixel iSight camera having 1.5 micron pixels, 1.2 megapixel photos and capability to capture 1080p HD at 60 fps.

The digital audio/video processor 218 can perform conversion between analog and digital and other necessary processing before storing the digital audio and video data in the memory 208 or an external storage medium or memory as an audio stream and video stream.

The controller 206 is the main processing unit for sending control signals and exchanging data with the other portions of the client device via, for example, the bus 212. The controller 206 can be a general purpose CPU or an application specific integrated circuit (ASIC). The memory 208 and controller 206 can be part of the ASIC. For example, if the client device 10 is a smartphone, the controller 206, memory 208, bus 212, interface 204 and digital audio video processor 218 will likely be integrated onto a single chip set, referred to as a system on chip (SoC), including a quad-core or dual-core CPU. It should be noted that the controller 206 can be alternatively configured to perform the A/D conversion, etc. so that the digital audio/video processor 218 can be eliminated.

As mentioned above, the memory 208 generally includes instructions for configuring the controller 206. In one case, the instructions can include a web browser which is executing code received via a connection to the network 15 and/or code stored locally on a client device and/or a device specific application stored locally at the client device. For example, in one case the client device can utilize a REST-like, REST-ful, and/or RPC based API for consuming services from a virtual machine on the server 106 as the manager device to generate the various graphical user interfaces discussed below. In this case, the client device 10 only executes instructions necessary for some of the steps of the charge capture system such as configuring the controller 306 to generate voice and image/video streams based upon data input via the microphone, camera and/or keyboard, and to send data packets including an audio stream representative of a voice utterance and a video stream or data stream representative of an image to the server 102 over a secure communication session. The server and/or server end modules associated with the manager device 20 can perform image parsing to extract PHI information from the image, render graphical displays on the client device 10 and return an acknowledgement message to the client device 10. Of course in another case, the instructions for generating the graphical user interfaces and parsing the PHI information from the image can be stored locally on the client device 10 or in combination with those at the server.

As mentioned above, one or more servers 106 provide charge capture manager device 20 and the database 102. As shown in FIG. 1B, the manager device 20 includes a transceiver 2002, a controller 2004 and memory 2006. The database 102 also includes a transceiver 1022, a controller 1024 and a memory 1026. The transceivers 1022, 1042 are configured to communicate via a connection to the network 105. The memories 1026, 2006 can be one or a combination of a variety of types of memory such as RAM, ROM, flash memory, DRAM or the like. Alternatively, although not shown, the database 102 can be a portion of the manager device 20. In this case, the memory 2006 can include instructions for the controllers 2004 to execute processes for providing the charge capture manager.

Figure 2C:
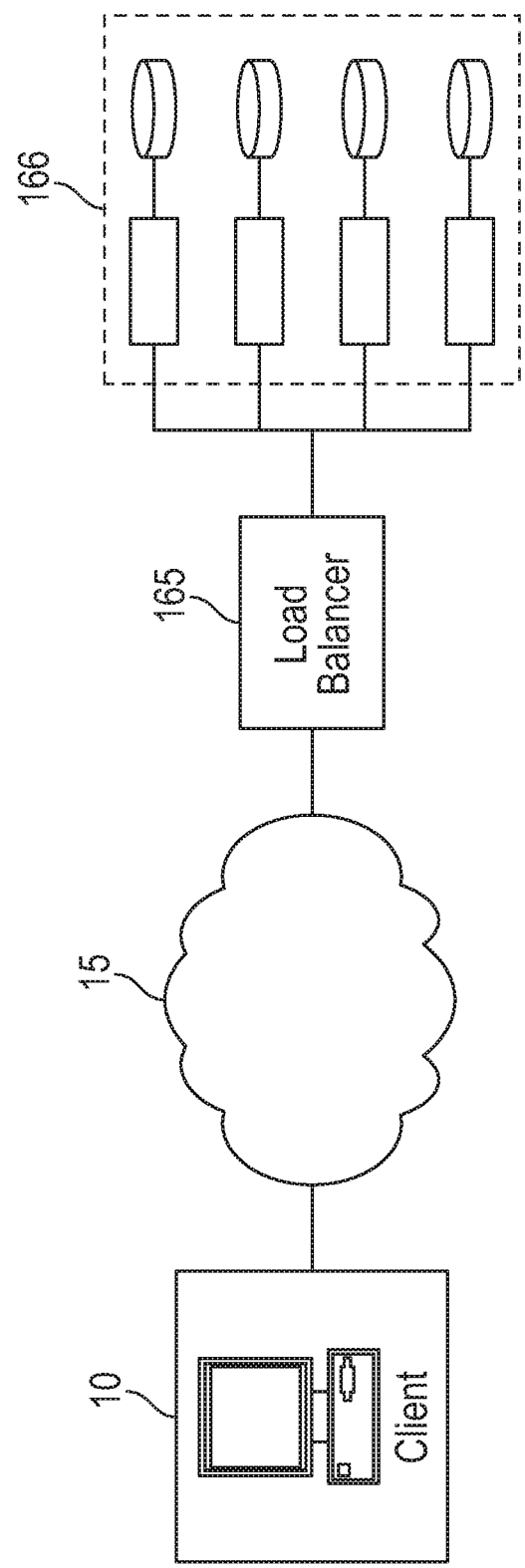
FIG. 2C is a block diagram illustrating exemplary portions of the system according to an alternative embodiment.

It should be noted that in FIG. 1, one server was shown merely for ease of illustration. However, as shown in FIG. 2C, the system can include a plurality of servers and databases 166 connected to the network 15 via a load balancer 165. The charge capture system can be implemented by performing X, Y and Z axis scaling of the hardware and software. Particularly, multiple virtual machine instances (VMs) can be running the manager applications behind the load balancer 165 on the different servers (X-axis), the servers can perform a functional decomposition to break up applications into small services (Y-axis), and each server (running the identical app) can be responsible for a subset of the data (sharing the database) broken up by something that logically makes sense for the business (i.e. patient last name, type of customer, etc.) with a component for routing (Z-axis).

Returning to the manager device 20, the memory 2006 includes instructions for configuring the controller 2004. For example, the controller 2004 and memory 2006 can be an ASIC or the instructions can be software. The memory 2006 can include instructions for configuring the controller 2004 to verify a resource request received by the transceiver 2002 from, for example, the client device 10. The resource request includes authentication credentials associated with a user name. Once verified, a secure communication session is established between the manager device 20 and the client device 10. The controller 2004 is configured to determine data in the database 102 such as bill history that is associated with a user name associated with the resource request. Further data can be stored in the database 102 associated with the user name while all or a predetermined portion of it is encrypted in accordance with a predetermined encryption protocol. The transceiver 2002 sends and receives encrypted data to and from the client device during the secure communication session possibly over SSL or TLS so it can be decrypted by the client device and presented in the graphical user interface to the end user.

Figure 8:
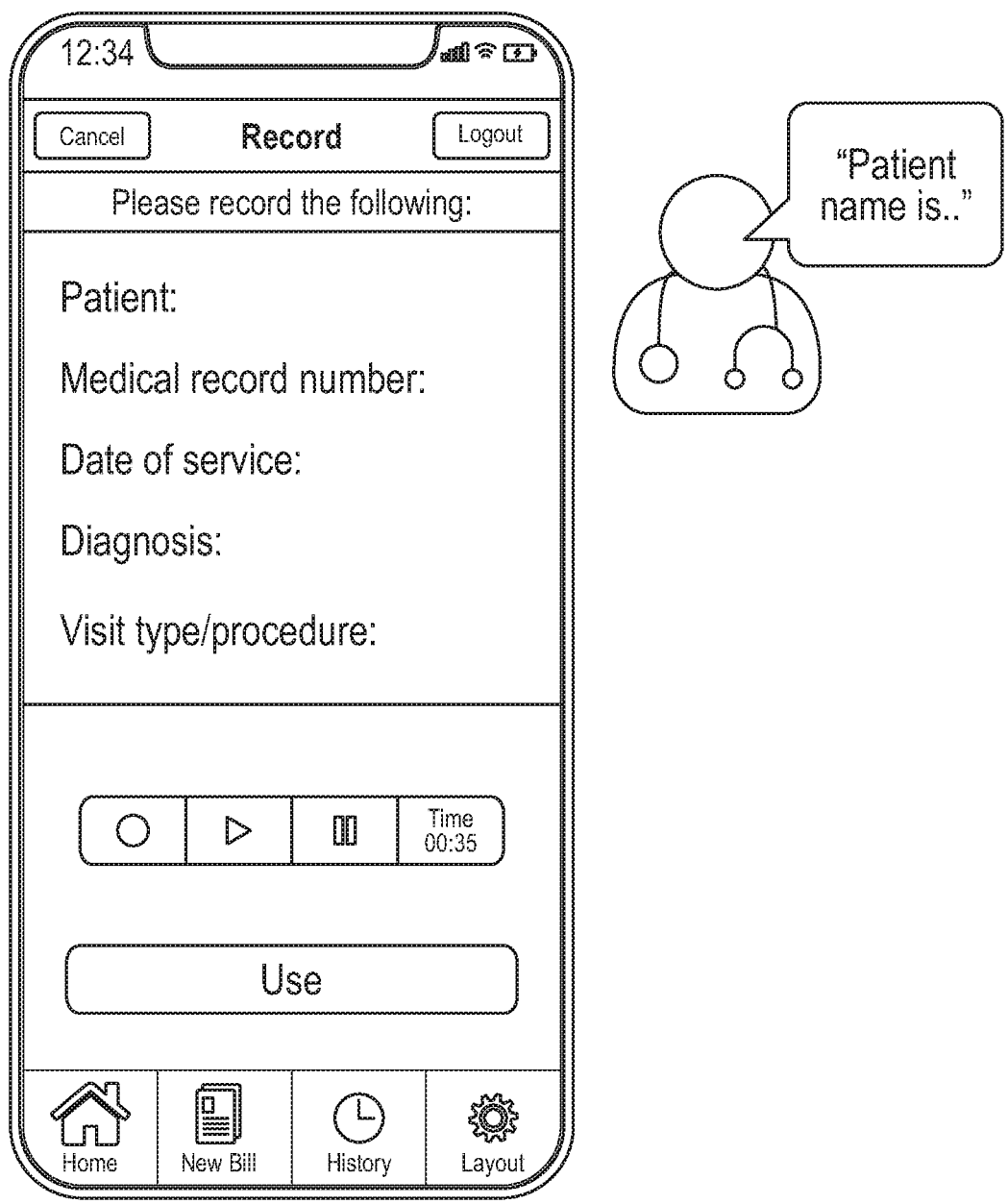
FIG. 8 illustrates a voice input display generated on the display of the client device during charge capture.
Figure 9:
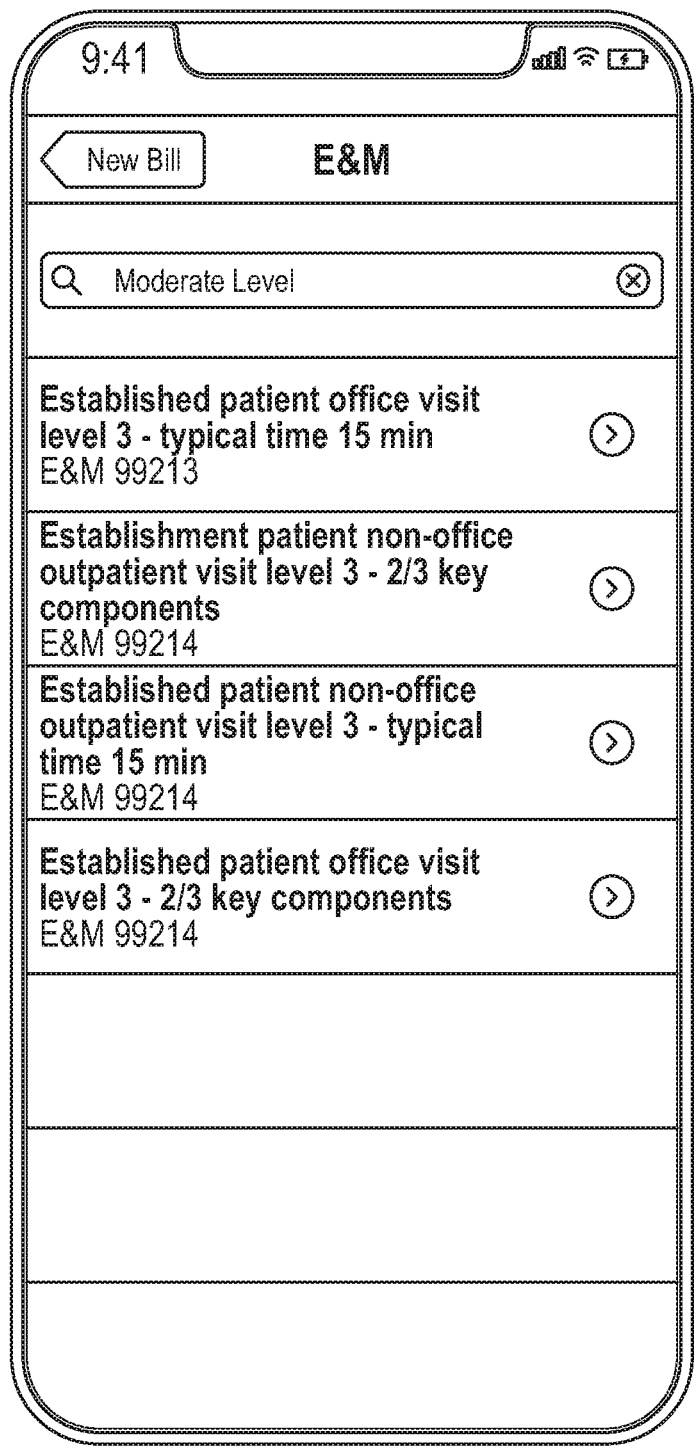
FIG. 9 illustrates an E/M code selection display generated on the display of the client device.
Figure 10:
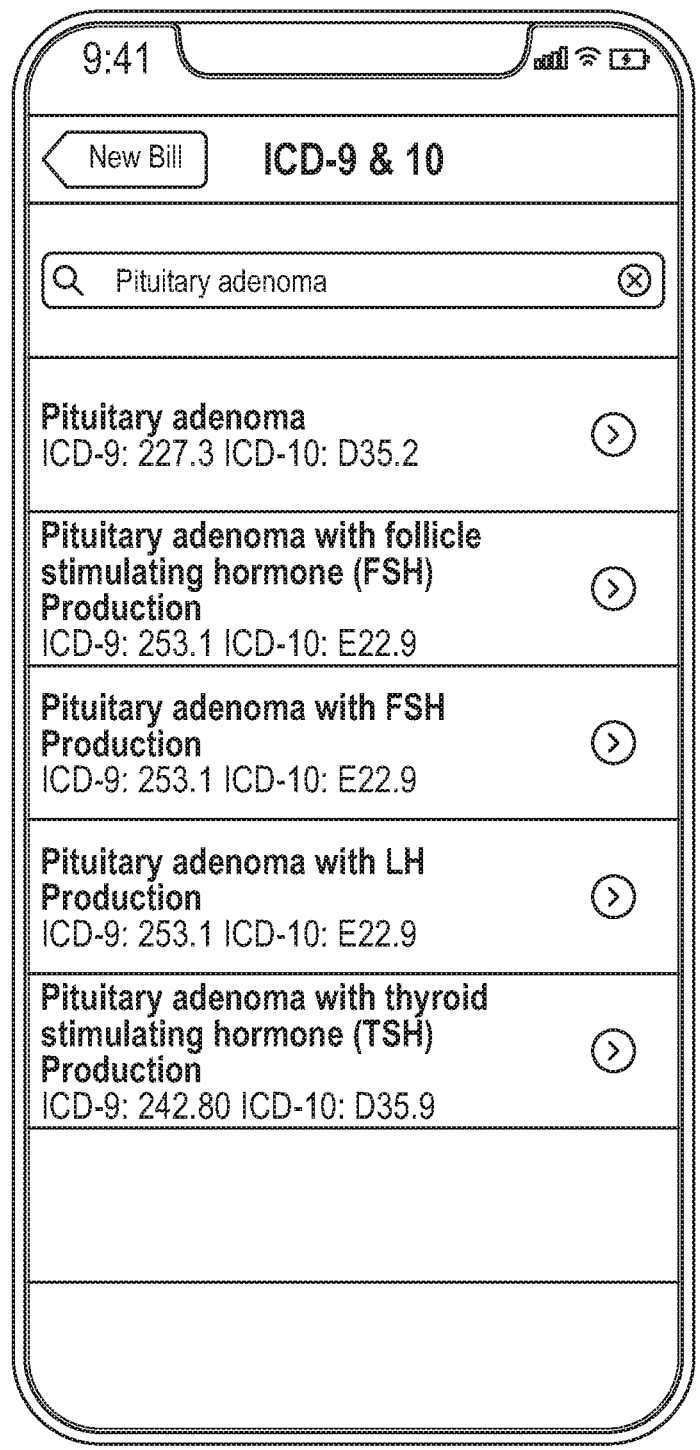
FIG. 10 illustrates a diagnosis selection graphical display generated on the display of the client device.

The memory 2006 includes instructions for configuring the controller 2004 to add a new bill data set received from the client device 10 to a bill history associated with the user and set a status flag associated with the data set to indicate new charge, the new bill data set including patient identification information, one or more diagnoses, one or more one or more evaluation and management codes, a procedure billing code, date information and user information in the data set. The instructions configure the controller 2004 to generate an acknowledgment message indicating successful transmission of the new bill data set to be sent to the remote client device 10, delete a data set indicated in a request from the client device 10, generate a notification message to be sent to another remote client device such as the biller indicating that the new bill data set has been stored; modify the status flag associated with the data set in response to a resource request received from the another remote client device including a request to change the status flag as shown in FIG. 8, and maintain an activity log of all access to a data set in the charge database.

The controller 2004 can be further configured to determine the bill history in the database 102 that is associated with the user name to be sent to the remote client device 10 during the secure communication session by the transceiver 2002, the bill history including one or more data sets, each of the one or more data sets including a patient identification of a patient for which a bill has been created, a medical record number and facility, date information regarding when a charge was submitted, and a current status of the charge.

During the secure session, the controller 2004 (and/or controller 206) is configured to generate various graphical displays to be rendered on the display of the client device for facilitating data capture. An exemplary scenario in which a user such as a physician uses the system to 'Touch, Talk, and Submit' billing data will be discussed with reference to FIGS. 3A-11. In this example, the client device 10 is a mobile device in which an application (mobile device app) is installed in the memory 1006. The controller 206 is configured according to the mobile device app stored in the memory 208. The controller 206 of the client device 10 executing the application generates a login screen to receive information for generating a resource request including an authentication credential associated with the user to be sent to the charge capture manager device 20 via the connection to the network 15. Upon being successfully authenticated, the transceiver 2002 of the manager device 20 is configured to receive the resource request to login the user.

The authentication process may be performed by using a certification authority who receives the user credentials. If the user credentials can be authenticated, the client device 10 receives authentication credentials such as a token issued by the certification authority. The client device 10 then generates a resource request including an authentication credential (the token) and a user name, and sends the resource request to the manager device 20. If the user credentials cannot be authenticated, the client device is returned to the login screen. The manager device 20 verifies the token by, for example, confirming that the certification authority that issued the token in the resource request is one of a number of predetermined trusted certification authorities.

After authentication, if necessary, the manager device 20 determines the data in the database 102 that is associated with the user name in the resource request. For example, the manager device 20 can retrieve a bill history and/or patient data that is associated with the user name in the database 102. The manager device 20 preferably encrypts the retrieved data according to an encryption protocol such as, for example, HMACsha256 secret key encryption and sends the encrypted data to the client device over SSL or TLS.

Figure 3A:
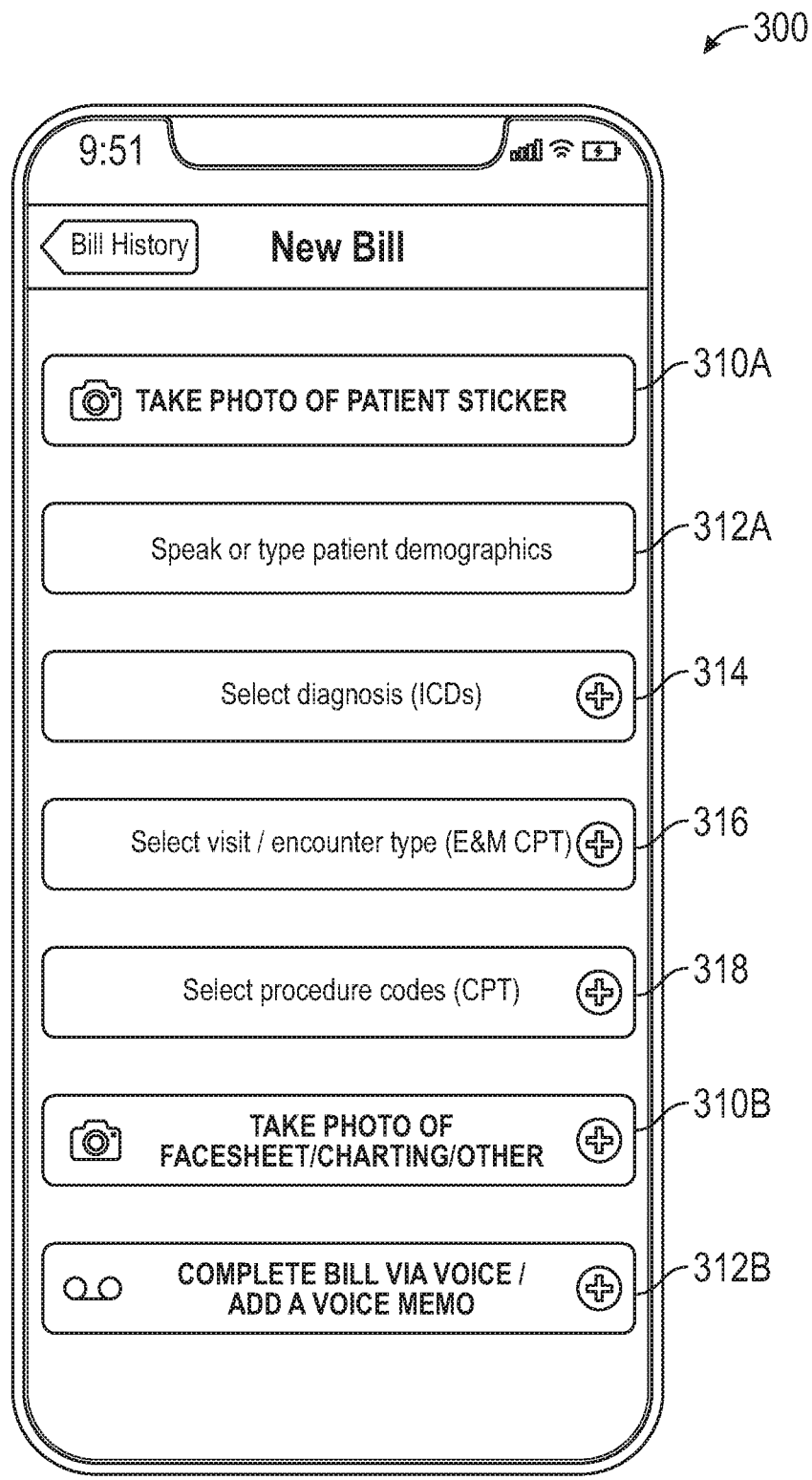
FIGS. 3A-3B illustrate an exemplary new bill graphical display generated on the display of the client device during charge capture.

Referring to FIG. 3A, a new bill graphical display 300 is generated on the display 320 of the client device 10. The display 300, as well as all the displays discussed below, can be generated by the controller at the manager device executing code at the server and sending the screen via a web browser and/or client device controller executing local code. The new bill graphical display 300 includes first and second image graphical interfaces 310A, 310B, a patient demographics graphical interface 312A, a diagnosis selection graphical interface 314, an evaluation and management (E/M) code selection graphical interface 316, a procedure code selection graphical interface 318 and a voice input graphical interface 312B. In this case, each of the graphical interfaces is a button. However, other appropriate interfaces can be used.

Figure 3B:
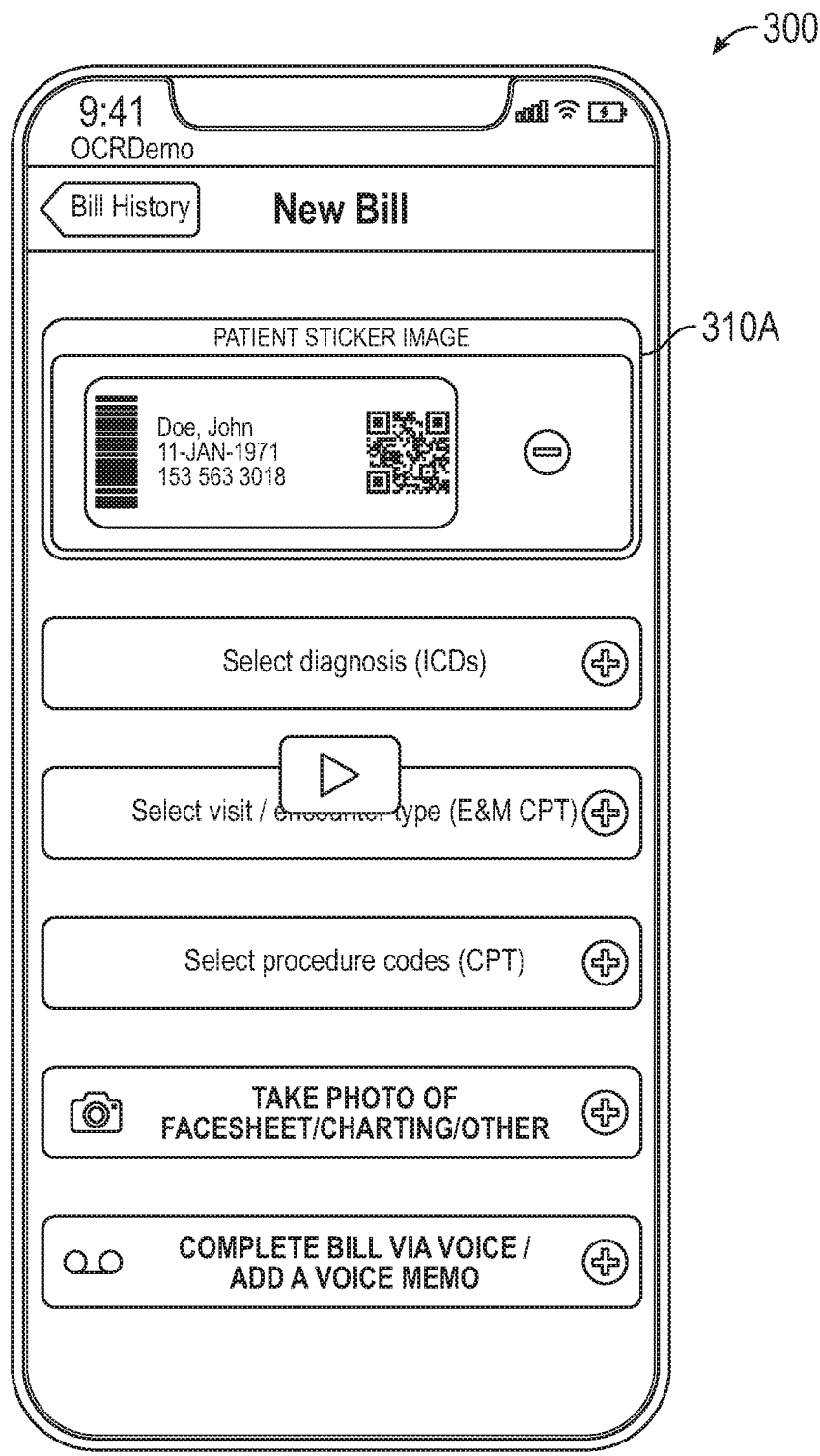
Figure 4:
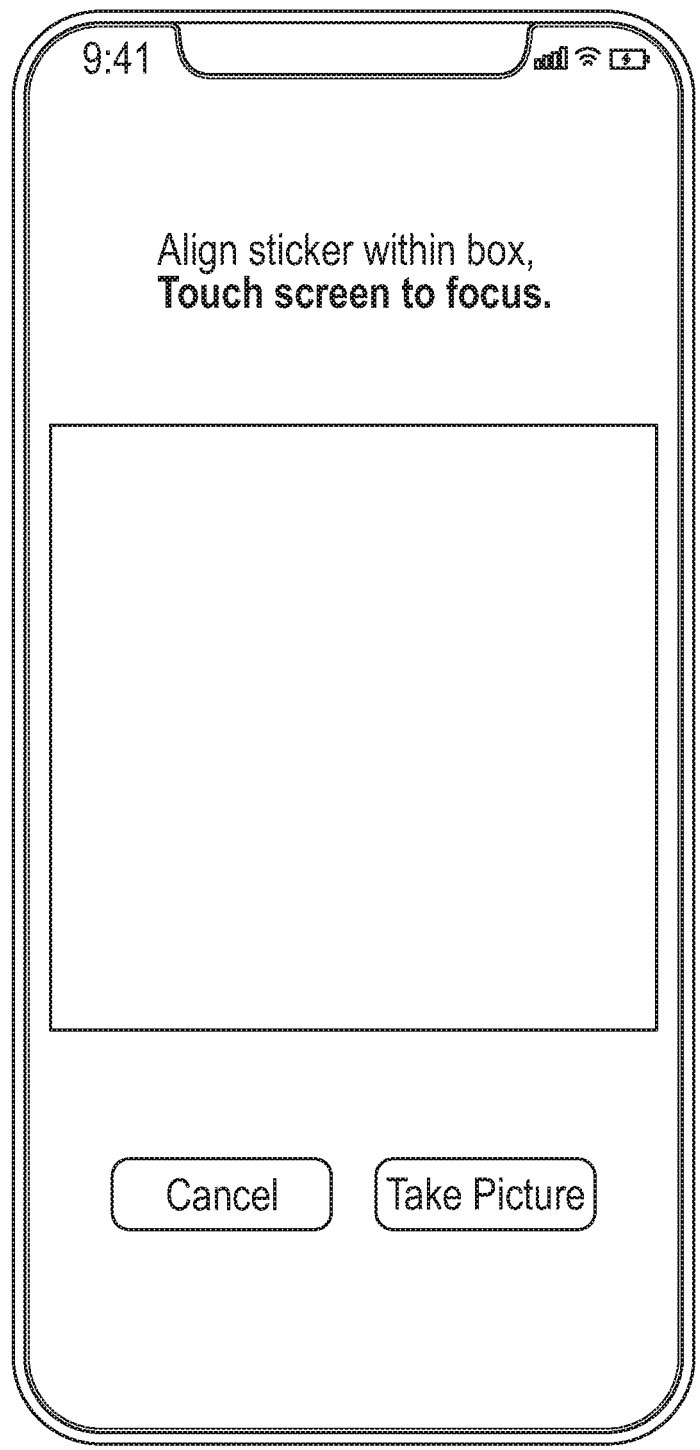
FIG. 4 illustrates an image input interface generated on the display of the client device during charge capture.
Figure 5A:
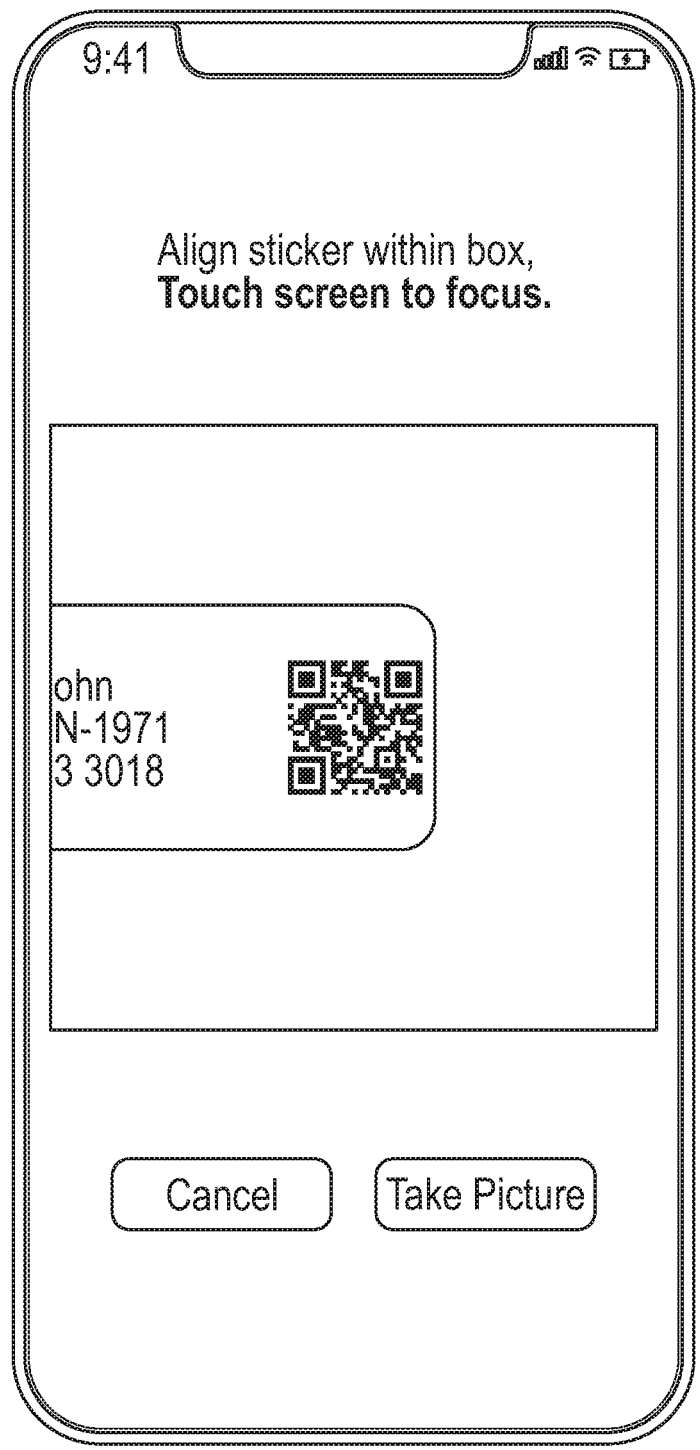
FIGS. 5A-5C illustrates an example of the image input interface being used to capture patient data from a patient sticker.
Figure 5B:
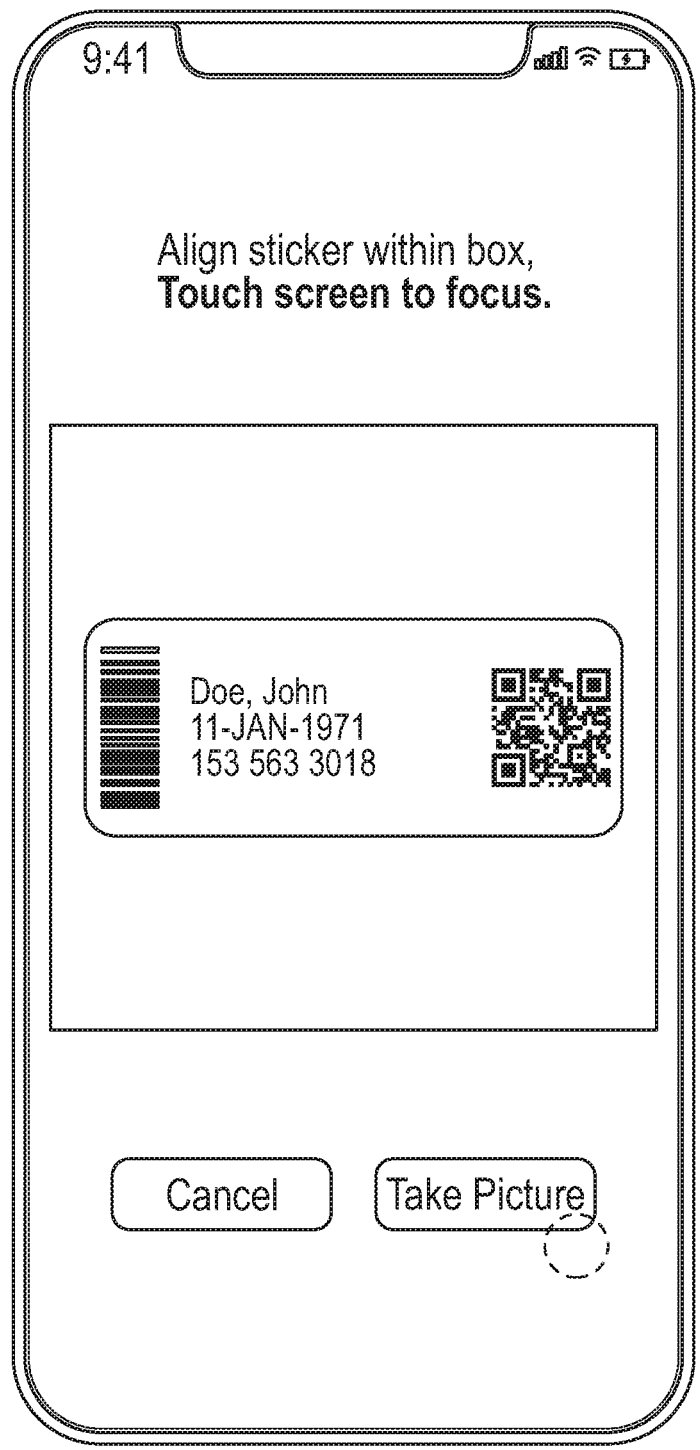
Figure 5C:
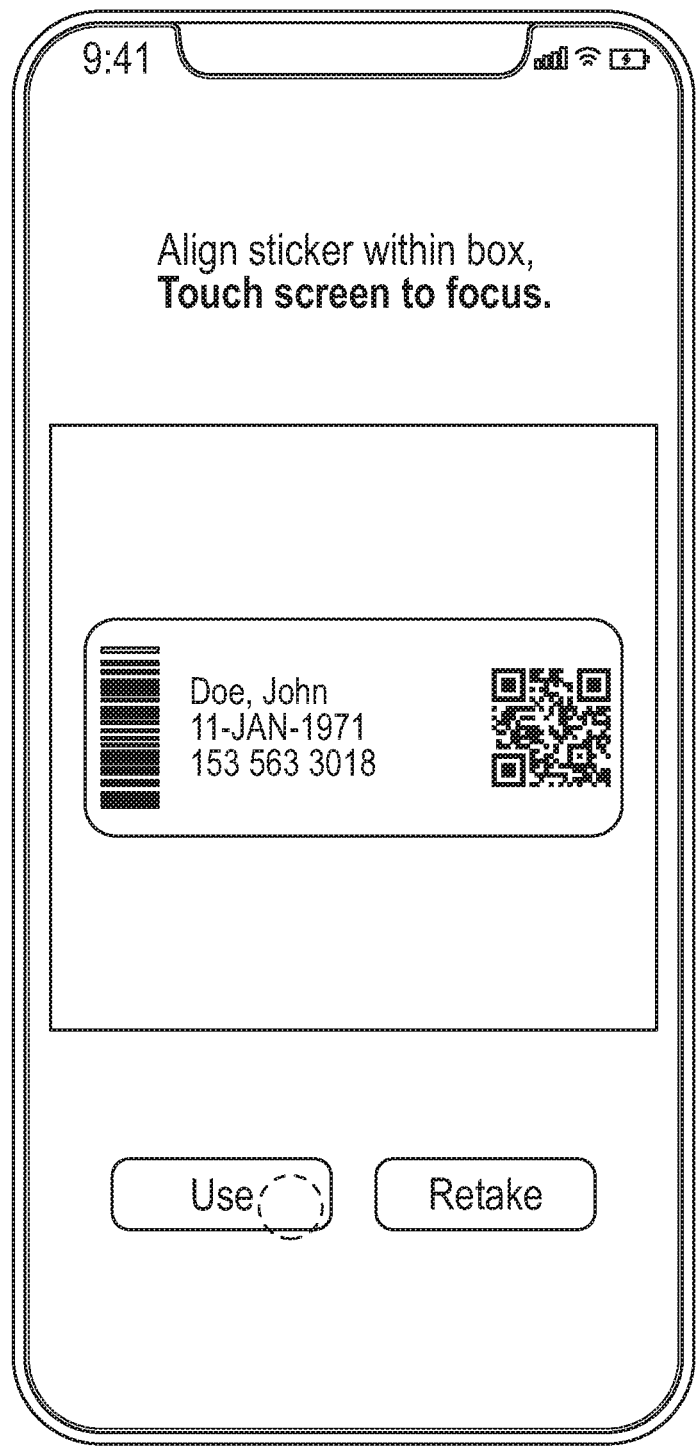
Figure 6:
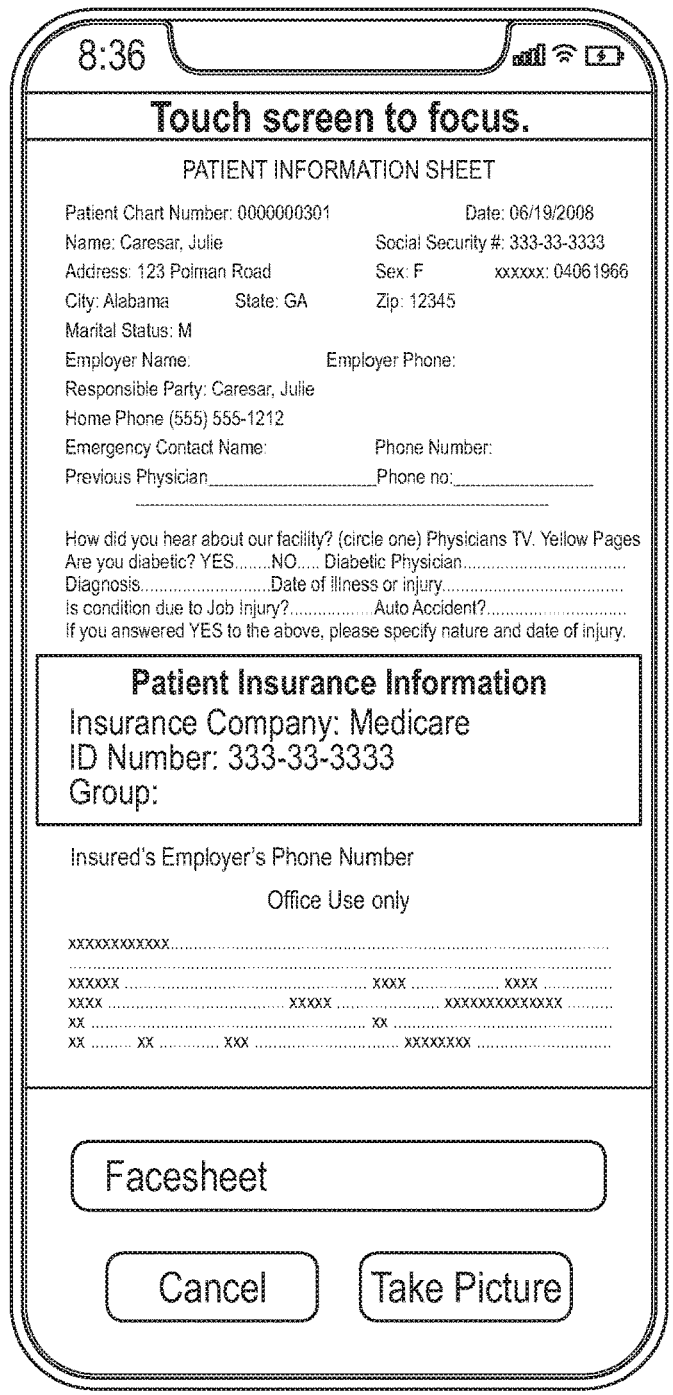
FIG. 6 illustrates an example of the image input interface being used to capture insurance data from a hospital face sheet.
Figure 7:
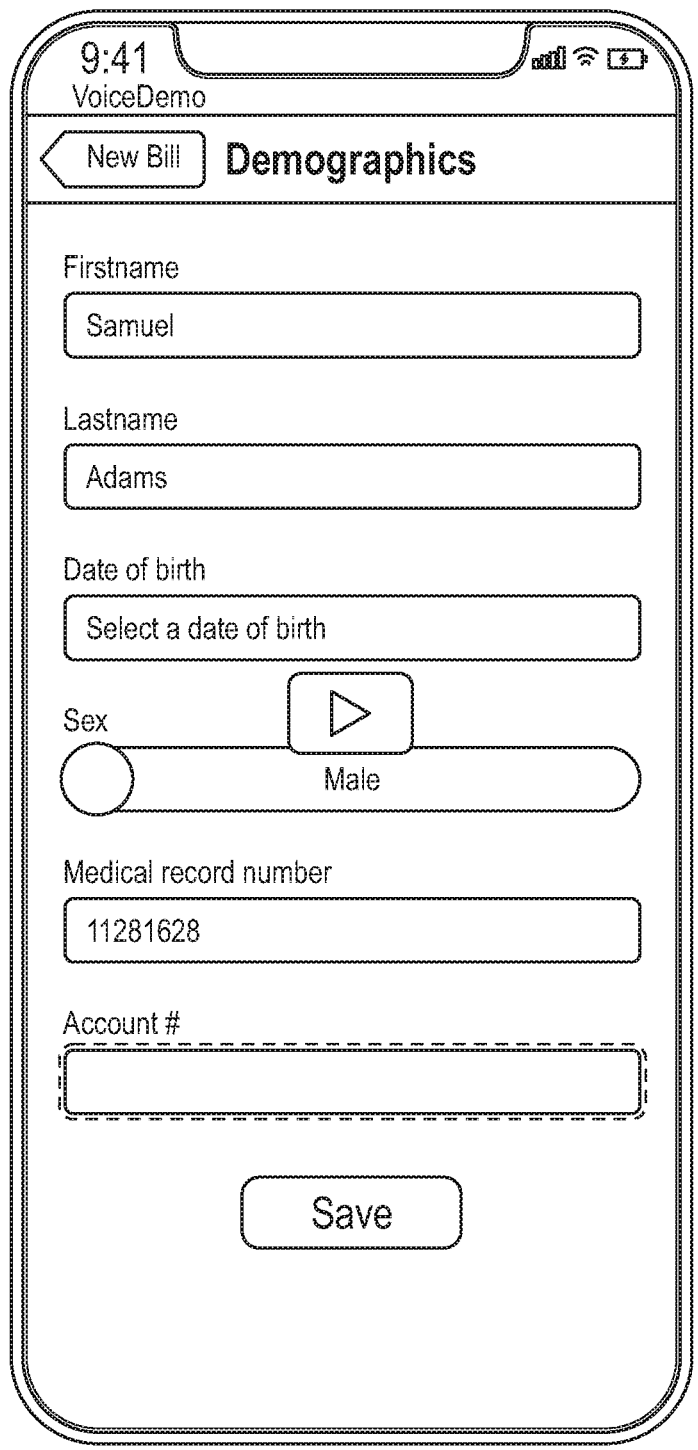
FIG. 7 illustrates a demographics display generated on the display of the client device.

The first and second image graphical interfaces 310A, 310B can be selected to parse PHI information from a photo of patient identification information such as, for example, a patient sticker or patient facesheet. When either of the first and second image graphical interfaces 310A, 312A is selected, an image input interface (shown in FIG. 4) is generated for receiving an image including patient identification information from the image and video input device 316, and a thumbnail of the image is subsequently displayed in the place of the selected interface. For example, as shown in FIG. 3B, a thumbnail of the patient sticker image appears in the area of the image graphical interface 310A.

When the voice input graphical interface 312B is selected, a voice input display subsequent in hierarchy to the new bill graphical display 300 is generated. The voice input display can include a record control graphical interface (FIG. 8) for activating the audio input device 314 to record voice utterances including patient identification information; a transcript display portion for displaying a transcript of the voice utterances; and a plurality of template graphical interfaces for categorizing information included in the voice utterances to extract the patient identification information.

Returning to FIG. 3A, when the patient demographics graphical interface 312A is selected, a demographics graphical display 320 (FIG. 7) subsequent in hierarchy to the new bill graphical display 300 is generated. Here, patient demographics and diagnosis information, can be entered manually, or via PHI extraction from the image or voice stream. For example, when the user speaks the account number to the microphone, the number is populated in the account # field. Moreover, if the account # is stored in the database, the manager device can pull the remaining demographic information from the database 120.

Returning to FIG. 3A, when the diagnosis selection graphical interface 314 is selected, the diagnosis selection display subsequent in hierarchy to the new bill graphical display is generated. The diagnosis selection display including: an open text field (FIG. 10) for receiving diagnosis related information; and a results display (for displaying a plurality of diagnosis codes returned as search results based upon the diagnosis related information. The diagnosis related information can be input by voice via the audio input device 314 and subsequently transcribed as described above.

When the E/M code selection graphical interface 316 is selected, an E/M code selection display (FIG. 9) subsequent in hierarchy to the new bill graphical display is generated. This display can be used to create or add an evaluation and management billing code, such as "new inpatient consultation". The E/M code selection display includes a plurality of selectable CPT codes obtained from, for example, the database 120 or one local to the client device 10. When the procedure code selection graphical interface 318 is selected, a procedure code selection display subsequent in hierarchy to the new bill graphical display 300 is generated. The procedure code selection display includes: an open text field for receiving procedure code related information; and a results display for displaying a plurality of procedure codes returned as results based upon the procedure code related information. The provider can use the procedure code selection to add the procedure information and the associated CPT billing code in the same manner, by speaking or selecting the appropriate procedure. In both code selection displays, billing codes can be picked from a list returned from a voice query.

The charge manager device 20 generates a new bill data set based upon the information received via the interfaces on the client device, stores the new bill data set to a bill history associated with the user in the database 120, and sets a status flag associated with the data set to indicate new charge. The new bill data set includes patient identification information, one or more diagnoses, one or more one or more evaluation and management codes, a procedure billing code, date information and user information. The instructions configure the controller 2004 to generate an acknowledgment message indicating successful transmission of the new bill data set to be sent back to the remote client device 10. Preferably, the manager device 20 deletes the data set indicated in the request from the client device 10. Further, the manager device can generate a notification message to be sent to another remote client device such as the biller indicating that the new bill data set has been stored; modify the status flag associated with the data set in response to a resource request received from the another remote client device including a request to change the status flag, and maintain an activity log of all access to a data set in the database.

Figure 11:
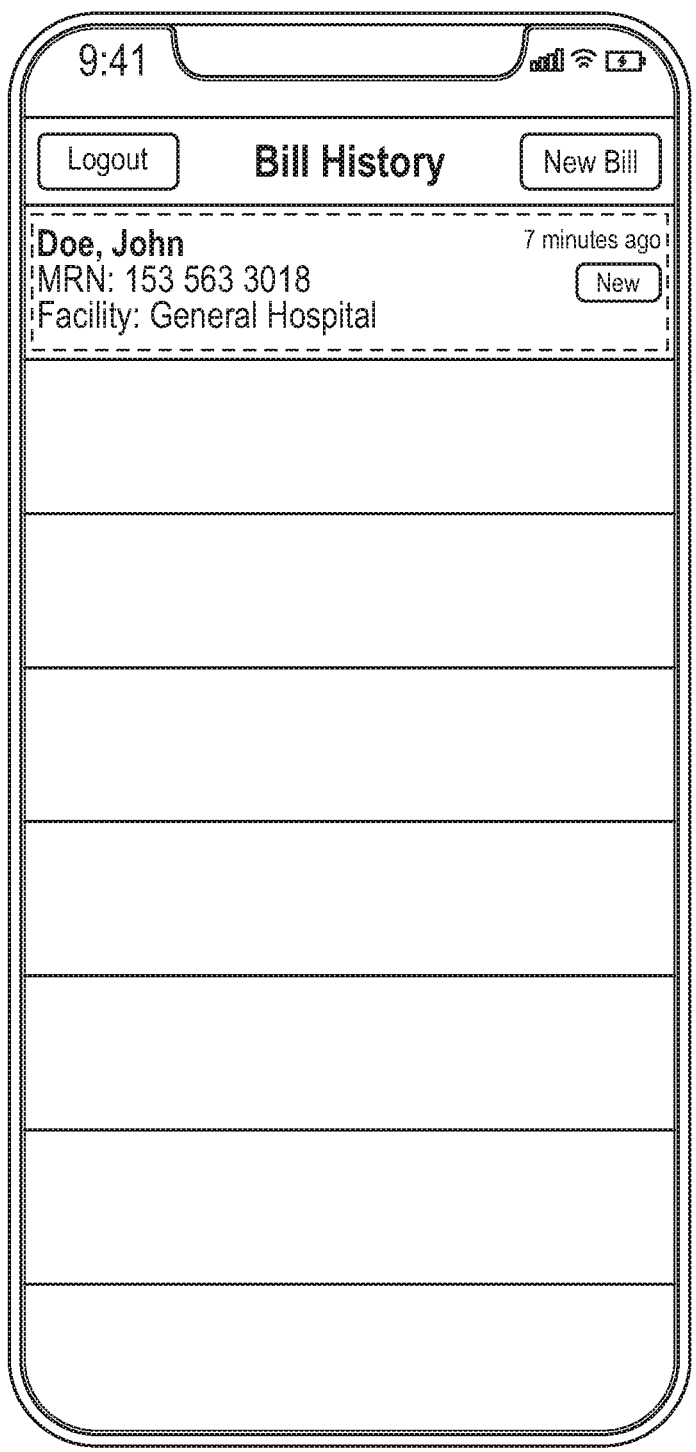
FIG. 11 illustrates a bill history display generated on the display of the client device.

Referring to FIG. 11, the controller 2004 can be further configured to determine the bill history in the charge database that is associated with the user name to be sent to the remote client device 10 during the secure communication session by the transceiver 2002. The bill history including one or more data sets, each of the one or more data sets including a patient identification of a patient for which a bill has been created, a medical record number and facility, date information regarding when a charge was submitted, and a current status of the charge. A bill history display can be generated on the client device displaying this information.

Following is a disclosure of an illustrative application of the invention, presented in the form of a demonstration and referring to the figures.

The system including the charge capture client device 10 and manager device 20 according to various embodiments eliminates the front end of the charge cycle, taking the charge lag of the physician revenue cycle from 10-30 days down to zero days. The client device 10 can be implemented by a mobile device such as smart phone or application on a desktop computer. The physician opens the mobile device or desktop app (application) and logs in. Particularly, the controller 306 of the client device 10 executing the application generates a resource request including an authentication credential associated with the physician (user) to be sent to the charge capture manager device 20 via a connection to the network 15. Upon logging in, one option the physician has is to view their bill history (FIG. 11) where they can see which patients (one or more patient identifications) they have created bills on, what the medical record number and facility were for those patients, when the charge was submitted and the current status of the charge, whether the biller has posted the charge to the practice management software and sent the charge off to the claims clearing house and then the payor, or whether the charge is still a new charge, thus allowing the doctor to have some direct visibility into the revenue cycle.

Most of the time, the provider is logging into the application on the client device 10 to do one thing, that is, create a new bill or charge. This is accomplished via the primary bill creation interface/workflow (new bill graphical display 300) for the doctor. This process can start with the ability to leverage the patient sticker or patient identification bracelet or wristband in the hospital to capture the demographics using computer vision. The doctor simply takes a photo of patient sticker after the doctor is prompted to take a picture of the patient sticker by the app. For example, the doctor centers the lens over the sticker and once satisfied, they take the picture. The doctor then has the opportunity to review the photograph, to perform quality assurance, to ensure that it is not blurry, etc. The doctor is prompted: 'can you read this?' If the doctor is satisfied and approves of the image quality, the doctor clicks the use (approve image) button and a thumbnail image of that patient sticker is then added to the bill. The thumbnail of the patient sticker image would then appear in the area of the image graphical interface 310A, 310B as shown in FIG. 3B.

If the doctor does not happen to be around or near a sticker, the doctor can always speak or type in the patient demographics. If the medical provider prefers voice to text technology, this can be used to create or capture the patient's basic demographics without touching the typewriter or keyboard on the device at all. The new bill graphical display 300 includes a voice input graphical interface (for inputting patient demographics 312A), (for inputting bill/memo 314B), wherein a voice input display subsequent in hierarchy to the new bill graphical display 300 is generated when the voice input graphical interface 112 is selected. The voice input display can include a record control graphical interface for recording voice utterances including patient identification information when selected; a transcript display portion for displaying a transcript of the voice utterances; and a plurality of template graphical interfaces for categorizing information included in the voice utterances to extract the patient identification information. An example of a doctor speaking a fictional patient's name and basic demographics would be "Jane . . . next field (navigating the data capture form in the user interface) . . . Doe . . . next field . . . female (adding the patient's gender) . . . next field . . . Nov. 1, 1942 (adding the patient's date of birth) . . . next field . . . 305862 (adding the patient's medical record number) . . . 688922 (adding the patient's account number)" The software application on the mobile device or desktop then transcribes the provider's verbal utterances. Once that process has been completed, those basic patient demographics have been populated in the app.

The provider then has the opportunity to select the related diagnoses for the visit, either by speaking into the client device or by selecting matching billing codes from a list of results that the software application returns in response to the doctor's verbal utterances. The new bill graphical display includes a diagnosis selection graphical interface 314, wherein a diagnosis selection display is generated when the diagnosis selection graphical interface 314 is selected, the diagnosis selection display subsequent in hierarchy to the new bill graphical display, the diagnosis selection display including: an open text field for receiving diagnosis related information; and a results display for displaying a plurality of diagnosis codes returned as search results based upon the diagnosis related information. For example, if the doctor speaks or selects "hypertension", a list of billing code search results is returned in response and then the doctor selects matching billing code. Here again the doctor can leverage voice to text to verbally look up the desired billing codes by speaking. The doctor can enter or add as many of the diagnosis billing codes as they need to by speaking or selecting, for example, "diabetes", and a list of billing code search results is returned in response. The doctor can continue with additional diagnoses to accurately capture what is going on with the patient ("obesity", "sprained right ankle", etc.).

Returning to FIG. 3A, then the doctor can select the evaluation and management (E/M) code selection graphical interface 316 to create or add an evaluation and management billing code, such as "new inpatient consultation". When the E/M code selection graphical interface 316 is selected, an E/M code selection display (FIG. 9) subsequent in hierarchy to the new bill graphical display is generated, the E/M code selection display including a plurality of selectable CPT codes. Anything in the billing code portion of the database (on the client device 10 or on the charge capture manager device 20) that matches what the physician has said or selected will be returned in the list of results in the pick list shown in the user interface in response to the physician's input. The doctor can then select the correct billing code. Again under ICD-9 not only is the ICD-9 diagnosis billing code provided, but also the corresponding ICD-10 diagnosis billing code. The present inventive solution is ICD-10 ready, which is a major issue, the transition from ICD-9 to ICD-10, facing hospitals and physicians. ICD-10 is slated to go live in October of 2014.

Finally, if a procedure was done on the patient during the encounter with the provider, the provider can select the procedure code selection graphical interface 318 so that the procedure code selection display subsequent in hierarchy to the new bill graphical display is generated. The procedure code selection display including: an open text field for receiving procedure code related information; and a results display for displaying a plurality of procedure codes returned as results based upon the procedure code related information. The provider can use the procedure code selection to add the procedure information and the associated CPT billing code in the same manner, by speaking or selecting the appropriate procedure. If the returned procedures are incorrect, the doctor can initiate the verbal billing search again without selecting a result from the list of billing codes returned in the last verbal billing code query. When the correct code is returned, it can be selected. Once the doctor is satisfied with the face sheet image quality after the provider's human quality assurance review, the approved image is then appended to the bill. If a doctor wants to add a memo, this also can be done verbally. For example, the doctor can speak "biller, please make sure we have captured the appropriate charges for the ankle splint that was provided to the patient period." The doctor then approves and saves the memo.

The next step is review of the bill information. The date of service is defaulted to today by the app. The date of admission can be added to the bill. The name of the doctor currently logged in is added. If the software user is billing for someone else, another doctor can be selected. The name of the facility can be added. The name of the referring doctor can be added. Once the user has entered the referring provider, the referring provider goes into the user's list of providers that are referring the user patients.

At this point the user is done and the user can hit submit. That bill goes into the user's bill history. The charge just created with its annotations, including images actually uploads in the background. The new charge is flagged as a new charge in the user interface. All charge data, including images, is securely transmitted and processed—structured data deriving from the patient information in the image submitted is created. The billing information is sent to the charge capture manager device 20.

After entry of information by the doctor, the biller can be notified that there are new charges. The biller logs in to the system (charge database in memory 2006 on the charge capture manager device 20) via a web browser and can see the charge the provider just created for 'jane doe.' The image derived patient demographics have been generated and the user can search, sort and filter the charges that users in the account have submitted based on the patient demographics and/or other information captured. The record from the list of submitted charges in the account provides a detail view of all of the information provided by the provider, including the transcript that was created by the provider for the billing staff. The billing staff has the opportunity to filter the bills based on status, and can change the status of the bills, can change what information is displayed and they can filter by user.

Thus, by using the mobile device, a doctor can improve workflow, capture more revenue and obtain payment faster by automating steps in the revenue cycle and eliminating inefficiencies, interim steps, and delays in information gathering (from multiple sources and physical locations) and submission. The invention accomplishes this by enabling on-the-go healthcare providers to capture and submit information about services rendered from any location via multiple modalities available on a mobile device. By using the technology, health care providers and healthcare provider organizations can accelerate clinical and administrative workflows, leading to more streamlined and timely medical claim generation and submission.

The system permits the collection of data utilizing multiple peripherals on a client device 10 such as a mobile device (including, but not limited to the microphone, accelerometer, video sensor, global positioning system, touch screen, keyboard) or peripherals that may be tethered to a mobile device or wirelessly communicate with a mobile device (i.e., a signal from another piece of electronic equipment) or utilizing the mobile device's ability to communicate (wirelessly or via wired connection) with an in house or third party information system. One potential application of the system is to collect data that documents and memorializes the occurrence of a billable medical encounter or episode of care between a provider and a patient or a billable service including but not limited the interpretation of a diagnostic study or review of the results from a diagnostic study. The system safely manages data that may contain personally identifiable health information that needs to be managed consistent with the HIPAA security and privacy rules and regulations Data Collection The data collected may be any combination of a multitude of types including, but not limited to:

All or a subset of the information that is necessary to collect for the purpose of activities including but not limited to: billing for medical services or procedures, assembling a medical claim, documenting the performance of medical services or procedures, preparing a report for presentation internally, to a third party, or to a patient, for record keeping and compliance purposes, for accreditation, for executing safety surveillance or quality improvement efforts, for participation in medical research or pharmaceutical post marketing surveillance;

Image based data that may contain written (handwritten or typescript) text or language that originated from a hard copy (i.e., a physical print out on a piece of paper) or a soft copy (i.e., an image rendered on a computer screen). For example, text data that might appear in clinical charting, diagnostic study reports, patient registration and insurance data, patient identification, legal contracts (i.e., advanced directives, procedure consent forms), questionnaires or feedback data provided by a person (i.e., a patient or a consultant);

Image based data that is the output of some diagnostic procedure such as a radiograph including, but not limited to one or a collection of plain film x-rays, computed tomography scans, magnetic resonance imaging scans, electrocardiograms, electroencephalograms, nuclear medicine studies, read outs rendered on the screen of various monitoring devices or a hardcopy thereof, data plotted on axes of some sort to demonstrate trends such as for example the change in the value of a vital sign over time, soft or hard copy reports and images from machines that may analyze a specimen originating from a patient (i.e., cluster of differentiation based immunophenotyping) or the amplification of a specimen from a patient (an example of the latter being a polymerase chain reaction and gel electrophoresis);

Image based data of a person, group of persons, or a particular part of a person or their anatomy or the condition thereof, including but not limited to an intraoperative image of a surgical site either with or without magnification (i.e., an image from an intraoperative microscope), image of a catheter, tube or line in place on a patient, image of a post-operative wound, image of a skin condition, image of a specimen (i.e., a surgical biopsy) either in gross or under low or high-power magnification such as that of an light microscope or electron microscope with or without staining, immunohistochemistry, immunofluorescence, etc.;

Verbal, or text data created generated by the end user of the technology (i.e., by using voice to text, handwriting, typing, searching a database of data on the client device 10, at the manager device 20 or another remote device and selecting items from the results to be added as annotations to the data being collected such as for example a medical diagnosis, evaluation and management, or procedure code);

Actively entered data (for example, information a user may provide by typing it into a form, by speaking, by interacting with and providing data via a software user interface via touch, voice or gestures) or passively collected data that the user has opted into providing or that the user is authorized to collect (i.e., the recording of a conversation, the users location as provided by global positioning system, the users movement such as that which may be provided by an accelerometer, etc.); and Information that is pulled from an information system that the user is authorized to access, that the user's mobile device (client device 10) is authorized to access and that the user's mobile device is able to connect to via a wired or non-wired connection. Examples may be accessing and pulling in patient or provider data from a hospital, a payor, a third party vendor system (i.e., credit scoring service, insurance validation service, etc.), pharmaceutical company database, a research database, an ontology database such as for example a database containing SNOMED data, using key words or search terms, or using record locators or identifiers captured by the mobile device's video sensor, captured by manual data entry (i.e., by typing or voice) by an end user, captured using physical characteristic or biometric data (i.e., image of an individual's face, a finger print, a retinal scan, using deoxyribonucleic acid, a protein sample, or analysis thereof).

The data captured via the various modalities can be temporarily securely stored on the client device 10 or transmitted, immediately or at a later date decided by the user or based on programmatic instructions, via a wired or non-wired connection in a secure fashion consistent with any organizational policies, HIPAA, or any other privacy or security laws.

The data may be transmitted securely to a (charge capture manager device 20) residing in a data center or another location. The data is securely managed by commercially reasonable means both in transmission and at rest in a fashion consistent with organizational policies, HIPAA, or any other privacy or security laws.

The data collected or a summary or subset thereof may at some point be transmitted securely to populate a third party system via an API or via a standard messaging protocol, including but not limited to Health Level Seven—HL7 messaging. An example of this might be transmission of the data to a practice management software being used to prepare claims to bill a payor for a medical service or procedure or transmission to a claims clearing house, in the case where the data has been organized and assembled into a medical claim.

The data can be organized, annotated, processed, analyzed, and synthesized throughout the process (i.e., during collection or after transmission, etc.). Feedback may be provided to the user about the data initiated by a machine driven by logic or feedback from a remote party interpreting or reviewing the data during or after its collection. Feedback might include but would not be limited to feedback on the quality of the data or the completeness of the data (i.e., notification about missing or outstanding data that still needs to be collected), conclusions determined and arrived at via analysis of the data collected and some other logic (business rules, clinical decision support, or any other algorithms), and/or suggestions about next steps that should be taken. Feedback may be delivered by a multitude of modalities via the mobile device including tactile, audio (speaker), visual (user interface) or other means One of the manners in which the inventive system described can be employed is as a means or interface between two organizations that need to securely transfer information including protected health information driven by a human or machine actor using a mobile device. The data transfer may be necessary for any authorized need including but not limited to a business need (i.e., medical billing and medical claims preparation), a compliance need, a quality monitoring need, an accreditation reporting need, a research need, and other needs.

Data may be actively captured or passively captured. Data may include, but is not limited to, data collected from manual data entry, from verbal data, from global positioning system data that may or may not be correlated with an action of the actor, from the current time (i.e., the actor's location where and time when a particular action was carried out or the location and time at which a particular event occurred), from images, such as, for example, snapshots of textual, graphical or pictorial data that is on a hard copy medium like paper, snapshots of similar information that is presented on a graphical user interface of some sort like a computer or workstation monitor, snapshots of a person, a part of a person, or a pathology of interest, snapshots of analytical readouts from specimens obtained from a patient or images of the patient specimen(s) under magnification with or without special dying or immunohistochemical staining, and/or snapshots of imaging studies (i.e. diagnostic imaging studies) that may be presented on a physical printout or as an image rendered on a computer or picture archival communications system (PACS) workstation).

Data may be collected at any location in one sitting, session, or episode or over a series of sessions, sittings, or episodes. Data collection locations might including but are not limited to, an office or business location, a residence, a skilled nursing facility, an acute care hospital, a rehabilitation hospital, an ambulatory surgery center, an outpatient clinic, a motor vehicle, a mobile clinic, a retail location, or other location.

Data may be collected by one individual or machine actor or collaboratively by multiple individuals and/or machine actors using mobile devices. Individuals may include, but are not limited to be employees of an organization, business associates and contractors of an organization, customers or patients of an organization, medical providers, among others.

Data is collected, annotated, assembled/organized, analyzed, processed, and submitted using various gestures (i.e., touch gestures) or verbal commands.

The mobile device 10 is equipped with multiple peripherals that enable data collection of numerous types, both passive (i.e., GPS position and event time) and active (snapshot images taken with the video sensor or data keyed in or added verbally as annotations to data collected). The actor (mobile healthcare provider) can utilize the video sensor on the device 10 to capture textual, graphical or pictorial data that may appear on a piece of paper (i.e., a hospital form or report like a 'patient sticker' or a patient 'face sheet' with patient identifiers and patient insurance information needed to bill the services), that may be in the form of a note that the healthcare provider hand wrote or typed and placed in the patient's paper or electronic medical record 'chart', that may be in the form of a snapshot of a patient, a wristband the patient may be wearing with personal identifiers and record locators, a part of the patient (face, surgical wound, site with a pathology that is being managed by the medical provider), or the patient in the midst of a procedure (i.e., an intraoperative image or snap shot of a fluoroscopic intra-procedure image that documents some aspect of the care—such as the procedure being done at a particular and correct anatomical site), that may be in the form of a diagnostic imaging or other study being reviewed on a workstation monitor or a hard copy on a light box (i.e., a film showing a particular finding on an imaging study). The actor may also annotate the images and other data with manual data entered into the mobile device 10 by voice, by typing on the device keyboard or by interacting with the software (stored in the memory 1006) on the mobile device 10 via the touch screen (i.e., adding some details of the services provided, adding a memo to be reviewed by a staff member or medical biller in the back office, searching for appropriate codes and then adding or annotating the data set with the diagnostic or procedure codes for the services provided). According to the above embodiments, the actor can use a client device 10 such as their own mobile device or an employer issued mobile device to collect, assemble, annotate and subsequently transmit this data (via transceiver 1002) to a data center in a remote location (charge capture manager device 20) where the information will be used by other actors or machines to execute downstream business processes. The manager device according to the above embodiments can securely manage (collecting, persisting, transmitting) the data set collected which, in this example would include personal health information and patient identifiers that need to be protected and managed securely by law.

The foregoing detailed description of the preferred embodiments has been presented only for illustrative and descriptive purposes and is not intended to be exhaustive or to limit the scope and spirit of the invention. The embodiments were selected and described to best explain the principles of the invention and its practical applications. One of ordinary skill in the art will recognize that many variations can be made to the invention disclosed in this specification without departing from the scope and spirit of the invention.

The invention claimed is:

1. A charge capture client device comprising:
a transceiver for communicating with a charge capture manager device via a connection to a network;
a controller coupled to the transceiver;
an imaging device coupled to the controller, the imaging device configured to capture an image including protected health information (PHI); and
a memory coupled to the controller, the memory including instructions to configure the controller to:
generate a new bill graphical display for facilitating user entry of a new patient data set, the new bill graphical display including:
an image graphical interface, wherein an image input interface is generated when the image graphical interface is selected for selecting an image captured by the imaging device so that the PHI information can be parsed from the image, the image graphical interface including a thumbnail image of the image after the image is selected;
a diagnosis selection graphical interface, wherein a diagnosis selection display is generated when the diagnosis selection graphical interface is selected, the diagnosis selection display subsequent in hierarchy to the new bill graphical display, the diagnosis selection display including:
an open text field for receiving diagnosis related information; and
a results display for displaying a plurality of diagnosis codes returned as results based upon the diagnosis related information;
an evaluation and management (E/M) code selection graphical interface; and
a procedure code selection graphical interface.

2. The charge capture client device of claim 1, wherein:
the imaging device is a camera or video sensor;
the image graphical interface includes a patient sticker image graphical interface and a patient facesheet graphical interface;
a patient sticker image input interface for inputting a patient sticker image is generated when the patient sticker image graphical interface is selected, the controller configured to parse the PHI information from the patient sticker image and change the patient sticker image graphical interface to include a thumbnail image of the patient sticker image; and
a patient facesheet image input interface for inputting a patient facesheet image is generated when the patient facesheet graphical is selected, the controller configured to parse the PHI information from the patient facesheet image and change the patient facesheet graphical interface to include a thumbnail image of the facesheet.

3. The charge capture client device of claim 1, wherein:
an E/M code selection display is generated when the E/M code selection graphical interface is selected, the E/M code selection display subsequent in hierarchy to the new bill graphical display, the E/M code selection display including a plurality of selectable Current Procedural Terminology (CPT) codes or Systematized Nomenclature of Medicine (SNOMED) descriptors that map to the CPT codes;
a procedure code selection display is generated when the procedure code selection graphical interface is selected, the procedure code selection display subsequent in hierarchy to the new bill graphical display, the procedure code selection display including:
an open text field for receiving procedure code related information; and
a results display for displaying a plurality of procedure codes returned as results based upon the procedure code related information;
the plurality of procedure codes of the procedure code selection display are CPT codes and descriptors or SNOMED descriptors that map to the CPT codes; and
the plurality of diagnosis codes are International Classification of Diseases (ICD) codes and descriptors or SNOMED descriptors that map to the ICD codes.

4. The charge capture client device of claim 1, wherein the controller is further configured to generate:
a voice input graphical interface, wherein a voice input display subsequent in hierarchy to the new bill graphical display is generated when the voice input graphical interface is selected, the voice input display including a record control graphical interface for indicating recording or streaming over the network data representing voice utterances including PHI information when selected.

5. The charge capture client device of claim 4, further comprising:
a microphone device for capturing the voice utterances, wherein the controller is further configured to initiate the microphone device to capture the voice utterance when the record control graphical interface is selected, and to generate one or more voice files including the voice utterances and temporarily store the one or more voice files in the memory.

6. The charge capture client device of claim 1, wherein:
the open text field for receiving diagnosis related information receives transcribed voice utterance as the diagnosis related information;
the controller is further configured to initiate a query based upon the diagnosis related information to be sent to the charge capture manager device, and to return billing codes based upon a response from the charge capture manager device.

7. A charge capture client device comprising:
a transceiver for communicating with a charge capture manager device via a connection to a network;
a controller coupled to the transceiver;
an imaging device coupled to the controller, the imaging device configured to capture an image including protected health information (PHI): and a memory coupled to the controller, the memory including instructions to configure the controller to:
generate a resource request including an authentication credential associated with a user to be sent to the charge capture manager device;
generate a data set including the PHI parsed from the image;
store one or more diagnoses in the data set;
store one or more evaluation and management codes in the data set;
store information about a procedure performed on the patient and a procedure billing code associated with the procedure in the data set;
encrypt the data set and store the encrypted data set in the memory to be transmitted to the charge capture manager device; and
delete the encrypted data set from the memory after receiving an acknowledgment message indicating successful transmission from the charge capture manager device.

8. The charge capture client device of claim 7, wherein the storing of the one or more diagnoses further comprises:
receiving voice data including diagnosis related information and returning a plurality of diagnosis codes based upon the diagnosis related information; and
receiving an indication of a selection of one or more of the plurality of diagnosis codes as the one or more diagnoses, wherein the plurality of diagnosis codes are International Classification of Diseases (ICD) codes or SNOMED codes and descriptors that map to a ICD codes.

9. The charge capture client device of claim 7, wherein the storing of the one or more evaluation and management codes includes:
receiving voice data including evaluation and management related information and returning a plurality of evaluation and management codes based upon the evaluation and management related information; and
receiving an indication of a selection of one or more of the evaluation and management codes as the one or more evaluation and management codes,
wherein the evaluation and management codes are Current Procedural Terminology (CPT) codes or SNOMED codes and descriptors that map to CPT codes.

10. The charge capture client device of claim 7, wherein the storing of the procedure includes:
receiving voice data including procedure related information and returning a plurality of procedure billing codes based upon the procedure related information; and
receiving an indication of a selection of one of the plurality of procedure billing codes as the procedure billing code,
wherein the procedure billing code is a CPT code or a SNOMED code that maps to a CPT code.

11. The charge capture client device of claim 7, wherein the controller is further configured to generate a bill history display based upon data received from the charge capture manager device in response to the resource request, wherein the bill history display includes one or more patient identifications for patients which bills have been created associated with the user or a group of which the user is a member, a medical record number and facility for each of the one or more patient identifications, diagnosis, evaluation and management and procedure billing code information, date information regarding when a charge was submitted, and a current status of the charge.

12. The charge capture client device of claim 7, wherein the controller is further configured to:
generate an image graphical interface, wherein an image input interface is generated when the image graphical interface is selected for selecting an image captured by the imaging device so that the PHI information can be parsed from the image, the image graphical interface including a thumbnail image of the image after the image is selected, the image graphical interface including a patient sticker image graphical interface and a patient facesheet graphical interface;

a patient sticker image input interface for inputting a patient sticker image is generated when the patient sticker image graphical interface is selected, the controller configured to change the patient sticker image graphical interface to include a thumbnail image of the patient sticker image; and a patient facesheet image input interface for inputting a patient facesheet image is generated when the patient facesheet graphical is selected, the controller configured to change the patient facesheet graphical interface to include a thumbnail image of the facesheet.

13. The charge capture client device of claim 7,
wherein the imaging device is a camera or video sensor;
wherein the controller is further configured to encrypt the image and send the encrypted image to the charge capture manager device where the encrypted image is decrypted and PHI is parsed from the image, and the controller is further configured to decrypt encrypted PHI received from the charge capture manager device.

14. A charge capture manager device comprising:
a transceiver configured to receive a resource request from a client device remote from the charge capture manager device, the resource request including authentication credentials associated with a user name;
a controller operatively coupled to the transceiver; and
one or more memory sources operatively coupled to the controller, the one or more memory sources including a charge database, billing code database and instructions for configuring the controller, wherein the instructions configure the controller to:
add a new bill data set in response to a request received from the client device to a bill history and set a status flag associated with the new bill data set to indicate new charge, the new bill data set including patient identification information, one or more diagnoses, one or more evaluation and management codes, one or more procedure billing codes, date information and user information in the data set;
generate an acknowledgment message indicating successful transmission of the new bill data set to be sent to the client device;
delete a data set indicated in a request from the client device; and
execute a billing code query in response to an authenticated and authorized user request from another charge capture client device.

15. The charge capture manager device of claim 14, wherein the controller is further configured to:
generate a notification message to be sent to the another charge capture client device indicating that the new bill data set has been stored;
modify the status flag associated with the data set in response to a resource request received from the another charge capture client device including a request to change the status flag; and
maintain an activity log of all access to resources on the charge capture manager device.

16. The charge capture manager device of claim 14, wherein the controller is further configured to determine the bill history in the charge database that is associated with the user name to be sent to the client device during the secure communication session by the transceiver, the bill history including one or more data sets, each of the one or more data sets including a patient identification of a patient for which a bill has been created, a medical record number and facility, date information regarding when a charge was submitted and medical service was provided, diagnosis, evaluation and management and procedure billing code information and a current status of the charge.

17. The charge capture manager device of claim 14, wherein the controller is further configured to decrypt an encrypted image received from the client device, parse protected health information (PHI) from the decrypted image and encrypt and send the parsed PHI to the client device.

18. The charge capture manager device of claim 14, wherein the controller is further configured to decrypt voice data received from the client device, generate a transcript from the decrypted voice data and send the transcript to the remote client device as encrypted data.

19. The charge capture manager device of claim 14, wherein the controller is further configured to search for and obtain billing codes for each of the one or more diagnoses, the one or more evaluation and management codes, and the one or more procedure billing codes in the billing code database based upon information included in the request from the client device, and return the obtained billing codes to the client device.

20. The charge capture manager device of claim 14, wherein the bill history includes PHI information parsed from an image.

* * * * *